US006755831B2

(12) United States Patent
Putnam et al.

(10) Patent No.: US 6,755,831 B2
(45) Date of Patent: Jun. 29, 2004

(54) WRIST SURGERY DEVICES AND TECHNIQUES

(75) Inventors: Matthew D. Putnam, Edina, MN (US); David Gesensway, Edina, MN (US); Charles D. Jennings, Great Falls, MT (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/996,784

(22) Filed: Nov. 30, 2001

(65) Prior Publication Data

US 2003/0105461 A1 Jun. 5, 2003

(51) Int. Cl.[7] .............................................. A61B 17/58
(52) U.S. Cl. ......................................... 606/69; 606/70
(58) Field of Search ............................. 606/60, 61, 69, 606/70, 71

(56) References Cited

U.S. PATENT DOCUMENTS

| | | | |
|---|---|---|---|
| 4,229,840 A | | 10/1980 | Gristina |
| 4,565,193 A | * | 1/1986 | Streli ........................... 606/69 |
| 4,653,487 A | | 3/1987 | Maale |
| 5,098,433 A | * | 3/1992 | Freedland .................... 606/63 |
| 5,100,405 A | | 3/1992 | McLaren |
| 5,197,966 A | | 3/1993 | Sommerkamp |
| 5,395,372 A | * | 3/1995 | Holt et al. ................... 606/61 |
| 5,514,137 A | | 5/1996 | Coutts |
| 5,586,985 A | | 12/1996 | Putnam et al. |
| 5,683,389 A | | 11/1997 | Orsak |
| 5,718,704 A | | 2/1998 | Medoff |
| 5,779,703 A | | 7/1998 | Benoist |
| 5,853,413 A | | 12/1998 | Carter et al. |
| 5,931,839 A | | 8/1999 | Medoff |
| 5,935,128 A | * | 8/1999 | Carter et al. ................. 606/69 |
| 6,096,040 A | | 8/2000 | Esser |
| 6,129,729 A | | 10/2000 | Snyder |
| 6,146,384 A | * | 11/2000 | Lee et al. ..................... 606/73 |
| 6,171,309 B1 | | 1/2001 | Huebner |
| 6,221,074 B1 | | 4/2001 | Cole et al. |
| 6,235,031 B1 | | 5/2001 | Hodgeman et al. |
| 6,283,969 B1 | | 9/2001 | Grusin et al. |
| 6,302,887 B1 | * | 10/2001 | Spranza et al. ............... 606/73 |
| 2001/0011172 A1 | * | 8/2001 | Orbay et al. .................. 606/69 |
| 2002/0032446 A1 | * | 3/2002 | Orbay ......................... 606/69 |
| 2002/0177850 A1 | * | 11/2002 | Bremer ........................ 606/70 |
| 2003/0083661 A1 | * | 5/2003 | Orbay et al. .................. 606/69 |
| 2003/0153918 A1 | * | 8/2003 | Putnam et al. ................ 606/69 |

OTHER PUBLICATIONS

O'Conner D.O. et al., "In vitro measurement of strain in the bone cement surrounding the femoral component of total hip replacements during simulated gait and stair–climbing," J. Orthop. Res. 14(5):769–777 (Sep. 1996).

Ballmer, Franz T., et al., "Treatment of Tibial Plateau Fractures With Small Fragment Internal Fixation: A Preliminary Report," Journal of Orthopaedic Trauma, vol. 14. No. 7, pp. 467–474 (Jan. 11, 2000).

De Ridder Victor A., et al., "Partridge Osteosynthesis: A Prospective Clinical Study on the Use of Nylon Cerclage Bands and Plates in the Treatment of Periprosthetic Femoral Shaft Fractures,", Journal of Orthopaedic Trauma, vol. 15. No. 1, pp. 61–65 (Aug. 19, 1999).

* cited by examiner

Primary Examiner—Eduardo C. Robert
(74) Attorney, Agent, or Firm—Fish & Richardson P.C., P.A.

(57) ABSTRACT

A fixation plate kit for fixation of a distal radius facture includes a fixation plate and a member. The fixation plate includes an elongated plate having a distal portion and a proximal portion. The distal portion includes a first surface, a second surface extending from and forming an angle with the first surface, and at least one first opening in the first surface. The proximal portion has a length and a width and is generally curved across its width over its length. The member is configured to be mounted in the first opening, extend from the first opening, and be inserted into a radius. The member may be integrally mounted in the first opening or may be an articulating member that extends from the distal portion over multiple angles and orientations.

19 Claims, 15 Drawing Sheets

GENERIC FRACTURE CLASSIFICATION
DISTAL RADIUS

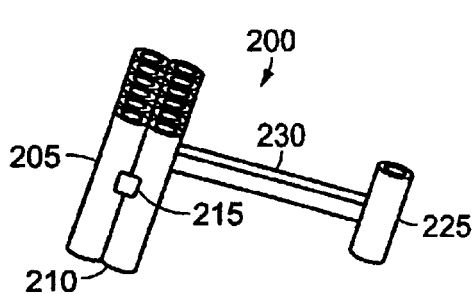 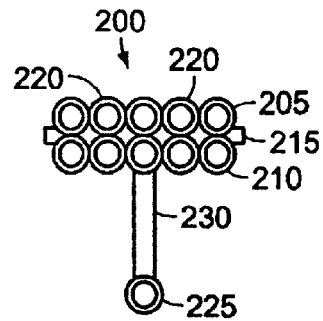
FIG. 16  FIG. 17
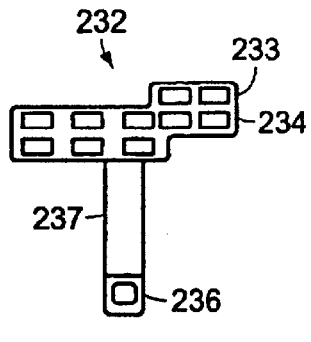 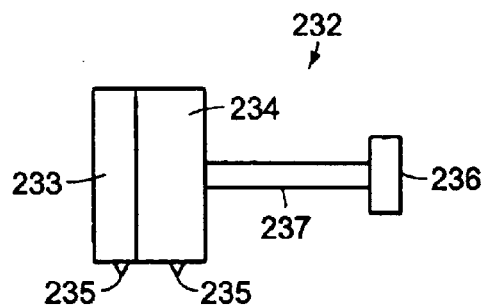
FIG. 18  FIG. 19
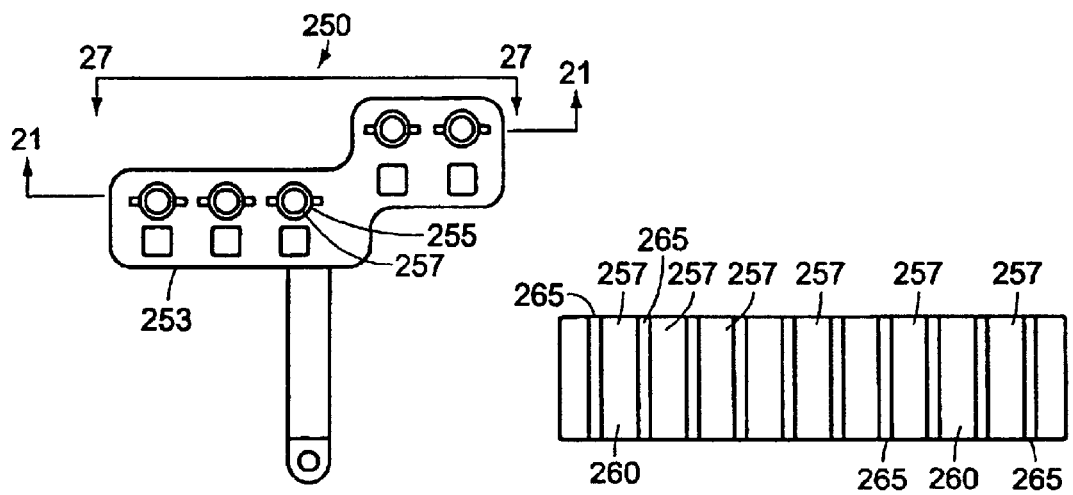
FIG. 20  FIG. 21

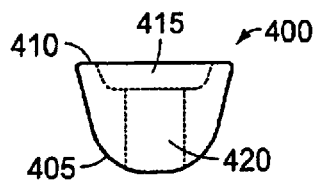
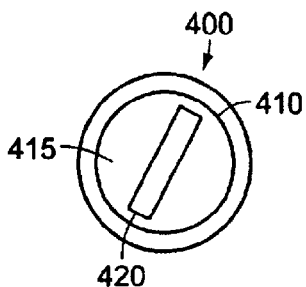
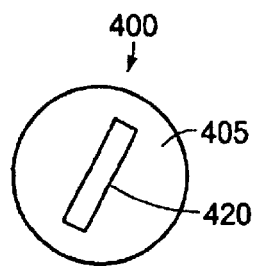
FIG. 35　　　　FIG. 36　　　　FIG. 37
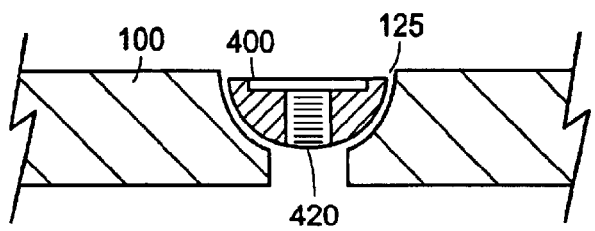
FIG. 38
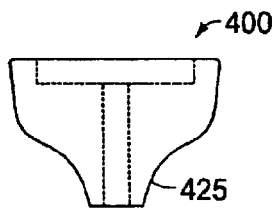
FIG. 39
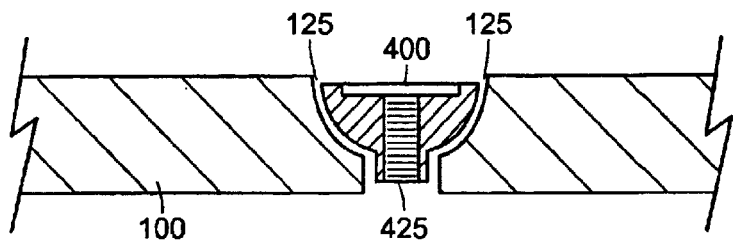
FIG. 40

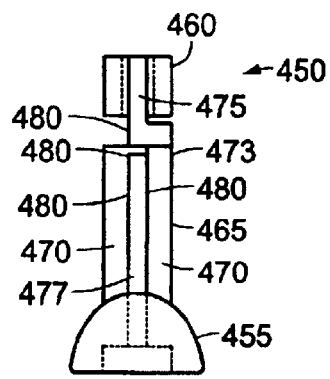
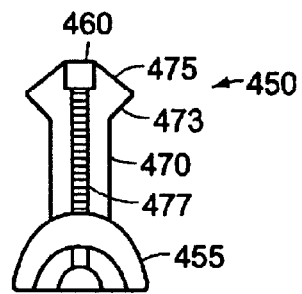
FIG. 41  FIG. 42
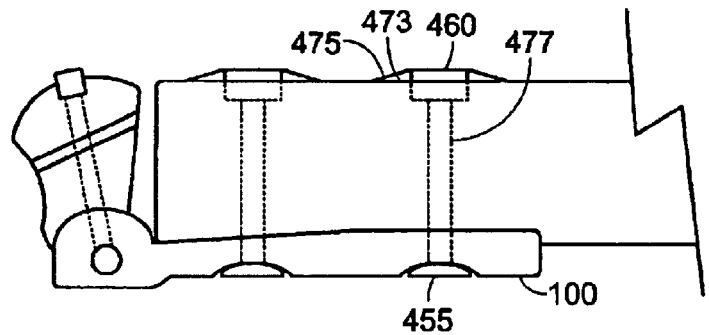
FIG. 43
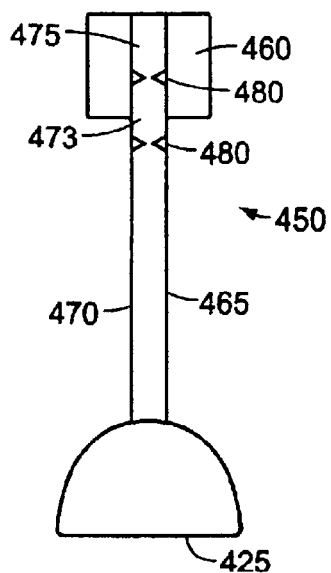
FIG. 44

WRIST SURGERY DEVICES AND TECHNIQUES

TECHNICAL FIELD

This invention relates to a surgical fixation device and techniques for its use, and more particularly to a tined fixation device and tined fixation device kit.

BACKGROUND

As illustrated in FIG. 1, the wrist joint 10 is formed at the intersection of the radius 15 and the ulna 20 with the metacarpals 25 and the carpals 30. The radius 15 includes an intramedullary canal 33 that runs the length of the radius. The canal 33 has a variable cross-sectional shape and cross-sectional diameter over its length. For example, the canal is wider and more oval shaped near the wrist joint but becomes rounded and narrower in the mid-region of the radius.

The wrist joint 10 and associated bones can be damaged, for example, in a fall. As illustrated in FIGS. 2a–d, a frequent injury to the wrist joint 10 is a distal radius fracture 35 in which a distal portion 40 of the radius is fractured away from the radius. Inherent bony instability, soft tissue damage, and frequent associated injuries make distal radius fractures very difficult to treat. Treatment of the fracture includes placement of a T-plate and external fixation, such as a cast. The functional outcome of the wrist joint after the treatment is generally directly related to residual deformity, both extra-articular alignment and intra-articular step-off, in the joint. FIGS. 2b–d illustrate various types of injuries according to the OTA classification system. For example, FIG. 2b illustrates a Type A injury, which occurs when the fracture line is along the plane of the epiphyseal plate. FIG. 2c illustrates a Type B injury, which occurs when the fracture line is along the margin of the joint. FIG. 2d illustrates a Type C injury, which occurs when the fracture line is along the plane of the epiphyseal plate, but also extends into the joint.

SUMMARY

In one general aspect, a fixation plate kit for fixation of a distal radius facture includes a fixation plate and a matching tensioning device. The fixation plate includes an elongated plate having a distal portion and a proximal portion. The distal portion includes a first surface, a second surface extending from and forming an angle with the first surface, and at least one tine extending from the first surface. The proximal portion has a length and a width and is generally curved across its width along its length and includes at least one opening configured to receive a tensioning device. The tensioning device is configured to pass through the opening in the proximal portion, through a channel in a radius, and to be tightenable to fix the proximal portion to the radius.

Embodiments of the fixation plate kit may include one or more of the following features. For example, the kit may further include a screw configured to be inserted into bone tissue and the distal portion of the fixation plate may include a second opening configured to receive the screw. The second opening may include a radiused circumference and the screw may include a curved gimbal head configured to articulate against the radiused circumference. The screw may be a bicortical or a unicortical screw.

The tensioning device may include a shaft having an interlocking interface, a head, and a moveable lock configured to move in one direction along the shaft towards the head. The head may have a curved surface configured to articulate in a curved surface of the opening in the proximal portion. The tensioning device may be a molly bolt.

The fixation plate kit may further include a guide for drilling holes in bone to place the tine. The guide may include at least one drill guide and at least one tine cover and the drill guide may be configured to receive, orient, and offset a drill bit in the same orientation as the tine when the tine is inserted into the tine cover. The drill guide also may include at least one opening and an insert configured to be received in the opening.

The fixation plate kit may further include one of more of a drill bit configured to drill a hole in bone tissue, written instructions for use, an instructional video, a tensiometer mounted to the tine and configured to measure a tension in the tine, a monitor configured to receive a signal that is indicative of strain in the tine and that is transmitted by the tensiometer, a screw driver, and/or an allen wrench.

The fixation plate may include a therapeutic agent. The therapeutic agent may include one or both of a bone growth regulating protein and a platelet derived growth factor. The therapeutic agent may be coated on or applied to the plate or applied directly on the injury.

In another general aspect, the fixation plate, the fixation plate kit, and the embodiments of the fixation plate and kit described herein are used to repair a distal fracture of the radius.

In another general aspect, a fixation plate kit for fixation of a distal radius facture includes a fixation plate and an articulating member. The fixation plate includes an elongated plate having a distal portion and a proximal portion. The distal portion includes a first surface, a second surface extending from and forming an angle with the first surface, and at least one first opening in the first surface. The proximal portion includes a length and a width and is generally curved across its width over its length. The articulating member is configured to be mounted in the first opening, articulated relative to the first opening to extend from the distal portion over multiple angles and orientations, and inserted into a radius.

Embodiments of the fixation plate kit may include one or more of the following features. For example, the first opening may include an outwardly extending rounded surface and the articulating screw may include a head having a concave articulating portion configured to articulate against the rounded surface. The articulating portion may have an elongated or hemispherical shape.

The fixation plate kit may further include a screw configured to be inserted into bone tissue and the distal portion of the fixation plate includes a second opening configured to receive the screw. The second opening may include a radiused circumference and the screw may include a curved gimbal head configured to articulate against the radiused circumference. The screw may be a bicortical or a unicortical screw.

The fixation plate kit may further include a tensioning device configured to pass through an opening in the proximal portion, through a channel in a radius, and to be tightenable to fix the proximal portion to the radius. The tensioning device may include a shaft having an interlocking interface, a head, and a moveable lock configured to move in one direction along the shaft towards the head. The head may have a curved surface configured to articulate in a curved surface of the opening in the proximal portion. The tensioning device may be a molly bolt.

The fixation plate kit may further include one or more of written instructions for use, an instructional video, a screw driver, an alien wrench, a drill bit configured to drill a hole in bone tissue, a guide for drilling holes in bone to place the articulating member, and a tensiometer mounted to the articulating member and configured to measure a tension in the articulating member. The guide may include at least one opening and an insert configured to be received in the opening.

The tensiometer may be configured to transmit a signal indicative of strain in the articulating member and the fixation plate kit may further include a monitor that is configured to receive the signal.

The fixation plate may include a therapeutic agent. The therapeutic agent may include one or both of a bone growth regulating protein and a platelet derived growth factor. The therapeutic agent may be coated on or applied to the plate or applied directly on the injury.

In another general aspect, the fixation plate with articulating members, the associated fixation plate kit, and the embodiments of the fixation plate with articulating members and kit described herein are used to repair a distal fracture of the radius.

In another general aspect, a fixation plate kit for fixation of a distal radius facture includes a fixation plate and a member. The fixation plate includes an elongated plate having a distal portion and a proximal portion. The distal portion includes a first surface, a second surface extending from and forming an angle with the first surface, and at least one first opening in the first surface. The proximal portion has a length and a width and is generally curved across its width over its length. The member is configured to be mounted in the first opening, extend from the first opening, and be inserted into a radius.

Embodiments of the fixation plate kit may include any of the features described above. For example, the member may be integrally mounted in the first opening or may be an articulating member that extends from the distal portion over multiple angles and orientations.

The details of one or more embodiments of the fixation device are set forth in the accompanying drawings and the description below. Other features, objects, and advantages of the invention will be apparent from the description, the drawings, and the claims.

DESCRIPTION OF DRAWINGS

FIGS. 16 and 17 are perspective and top views, respectively, of a drill guide for use with the tined fixation device of FIG. 3.

FIGS. 18 and 19 are top and side views, respectively, of a second embodiment of a drill guide for use with the tined fixation device of FIG. 3.

FIG. 20 is a top view of a drill guide with removable drill inserts.

FIG. 21 is a cross-sectional side view of the drill guide of FIG. 20 taken along section line 20—20.

FIGS. 35–37 are side, top, and bottom views, respectively, of a fastener.

FIG. 38 is a cross-sectional side view of the fastener of FIG. 35 positioned within a fixation device.

FIG. 39 is a side view of a fastener with an extended base.

FIG. 40 is a side view of the fastener of FIG. 39 positioned within a fixation device.

FIGS. 41 and 42 are front and side views, respectively, of a molly bolt system for retaining the fixation device of FIG. 3 to a bone.

FIG. 43 is a side view of the molly bolt system of FIG. 41 used to retain the fixation device to a radius.

FIG. 44 is a side view of a second embodiment of a molly bolt system.

Like reference symbols in the various drawings indicate like elements.

DETAILED DESCRIPTION

Referring to FIGS. 3–9, a tined fixation device 100 is configured to be used in surgical procedures to fix bone fragments and an adjacent bone in a rigid fixation. The tined fixation device 100 is specifically configured for dorsal, left wrist fixation. The tined fixation device 100 includes a first or proximal section 105 and a second or distal section 110 from which tines 115 and 120 extend.

Figure 8:
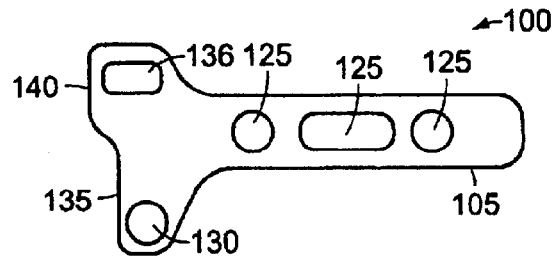
FIGS. 8 and 9 are top and bottom views, respectively, of the tined fixation device of FIG. 3.
Figure 9:
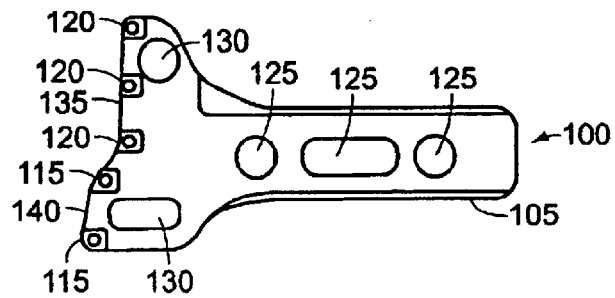
Figure 10:
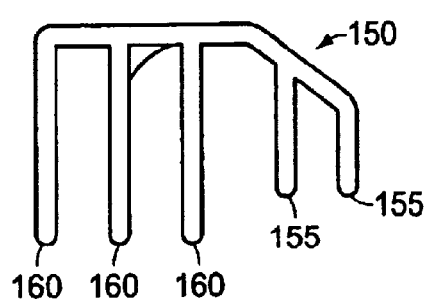
FIGS. 10 and 11 are front and end views, respectively, of a tined fixation device for fixation of a right wrist fracture.
Figure 11:
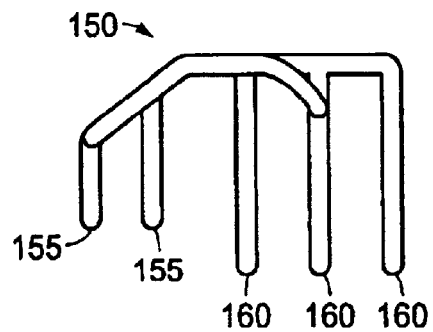
Figure 12:
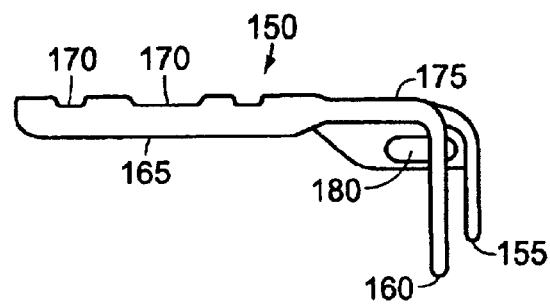
FIGS. 12 and 13 are side views of the tined fixation device of FIGS. 10 and 11.
Figure 13:
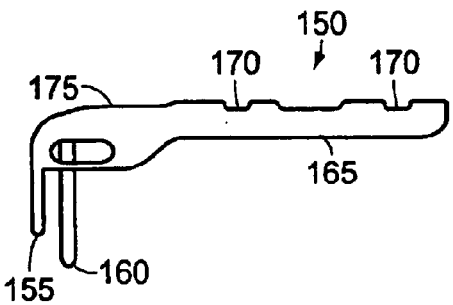
Figure 14:
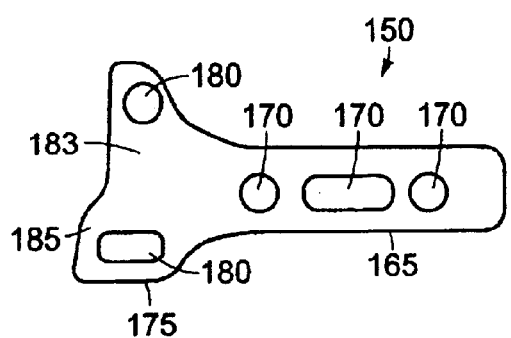
FIGS. 14 and 15 are top and bottom views, respectively, of the tined fixation device of FIGS. 10 and 11.
Figure 15:
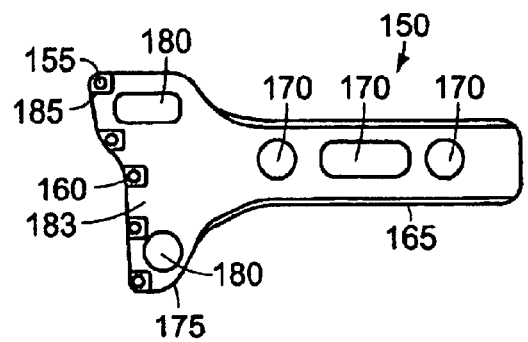
Figure 22:
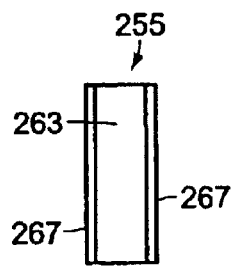
FIGS. 22 and 23 are side views of a drill insert for insertion into the drill guide of FIG. 20.
Figure 23:
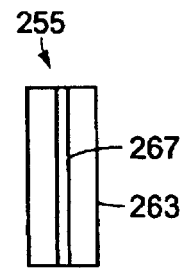
Figure 24:
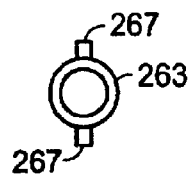
FIG. 24 is an end view of the drill insert of FIG. 22.

The first section 105 is generally elongated, narrower than the second section 110, and includes one or more openings 125. The openings 125 are used to mount the first section to the radius, and may be round, elongated, and/or of any other shape and of varying sizes. For example, FIGS. 8 and 9 illustrate that the openings 125 in the first section 105 can be configured as a pair of round openings and an elongated opening. The elongated opening provides flexibility for screw placement. The openings 125 also may be oversized to allow screws to be angulated and countersunk full thickness for a low profile. The first section 105 has a curved shaped across its width that is designed to generally follow the typical curve of a radius on which it will be mounted so that the first section will be stably seated against the radius.

The second section 110 forms a T with the first section 105 and has a curved shape that follows the dorsal portion of the radius. The second section 110 also includes openings 130, a first portion 135, and a second portion 140. The first portion 135 is flat such that it generally follows the shape of the anterior portion of the dorsal portion of the radius and the second portion 140 is curved such that it generally follows the shape of the lateral portion of the distal portion of the radius. The tines 115 and 120 extend from the second section 110. Although FIGS. 3–9 show the tines 115 and 120 extending from the end of the second section 110, the fixation device 100 can be configured with the tines extending from a more central portion of the second section such that the second section extends beyond the tines to add stability to the dorsal portion of the radius.

Figure 6:
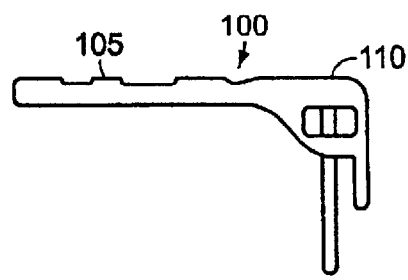
FIGS. 6 and 7 are side views of the tined fixation device of FIG. 3.
Figure 7:
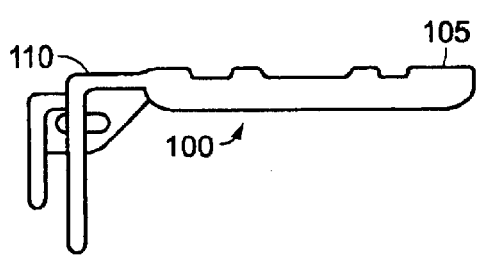

The first portion 135 does not extend as far as the second portion 140 and, consequently, the tines 115 and 120 extend from the fixation device 100 in a staggered or lateral offset manner, as best seen in the side views of FIGS. 6 and 7 and the bottom view of FIG. 9. In this example, the fixation device 100 is configured to have three tines 115 extend from the first portion 135 and two tines 120 extend from the second portion 140. The length of the tines 115 and 120 are set to correspond to the thickness of the dorsal portion of the radius such that the tines can be as long as possible to provide the maximum fixation and stabilization. For example, the tines 115 are longer than the tines 120 because the anterior portion of the dorsal portion of the radius is thicker than the lateral portion of the dorsal portion of the radius.

Referring to FIGS. 10–15, a tined fixation device 150 designed for implantation on a right wrist includes a pair of tines 155 and three tines 160, a first section 165 having openings 170, and a second section 175 having openings 180. The first section 165 is curved similarly to the first section 105 of device 100. The second section 170, like the second section 110 of the device 100, includes a first portion 183 and a second portion 185. The tines 155, 160 extend from the second portion 185.

As illustrated in FIGS. 3–15, the tined fixation device 150, which is designed for implantation on the right wrist, differs as a mirror image version from the tined fixation device 100, which is designed for implantation on a left wrist. Specifically, on the right wrist fixation device 150 the pair of tines 155 are in an offset position to support the scaphoid fossa of the right wrist and the three tines 160 are positioned to support the lunate fossa of the right wrist. On the left wrist fixation device 100 the oppositely placed (relative to the device 150) tines 120 are positioned to support the scaphoid fossa of the left wrist and the tines 115 are positioned to support the oppositely placed (relative to the device 150) lunate fossa of the left wrist. Because of the irregular, non-symmetric shape of the head of the distal radius, the fixation devices are configured differently to take advantage of the lack of symmetry. Specifically, the lateral offset of the tines provides improved rotational control of the bone fragment(s). Moreover, the offset provides a surface on the device adjacent to the tines 120 through which an opening can be located, which provides additional rotational control of the bone fragment. Although a universal tined, fixation plate can be designed for use on either the left wrist or the right wrist, it would lack the features of the devices 100, 150 that improve their function on the specific wrist.

The device 100, 150 can be fabricated from a biocompatible metal, such as stainless steel or titanium, using any known method. For example, as described in U.S. Pat. No. 5,586,985 to Putnam, which is incorporated herein in its entirety by reference, the device 100, 150 can be fabricated by machining from a solid piece of metal or by forming from a sheet by bending and pressing-forming. It also can be fabricated by stamping, casting, or using any other known technique. The dimensions of the device can be approximately 1.5 mm thick, have a width of approximately 12 mm at the proximal end 105, and have a width of approximately 24 mm at the distal end 110. The tines can be generally square shaped with a dimension of approximately 2 mm per side to provide sufficient strength to the tine. The tines 115, 155 are positioned approximately 55 mm from the proximal end 105, 165 and the tines 120, 160 are positioned approximately 3 mm away from the tines 115. The openings in the device can have, for example, a diameter of 4.5 mm and be countersunk full thickness to a 6 mm head to allow for angulation. These dimensions can be modified to accommodate the variations between patients due to factors such as age, height, weight, and gender.

To mount the fixation device to a radius, holes are drilled in the radius to receive the tines. Although the holes can be drilled in a free-hand manner, referring to FIGS. 16 and 17, a drill guide 200 optionally may be used to drill holes that are accurately aligned with the configuration of the fixation device 100 and, more specifically, the configuration of the tines 115 and 120. The drill guide includes a first set of tubes 205, a second set of tubes 210 or tine covers, a stabilizer bar 215, guide pins 220, a tube 225, and a connector 230 that connects the tube 225 to the second set of tubes 210. Each set of tubes 205 and 210 is arranged to resemble the arrangement of the tines 115 and 120; however, the first set of tubes and the second set of tubes are slightly offset. The first set of tubes 205 is configured to receive drill bits when the tines 115 and 120 are inserted into the second set of tubes 210 such that drill holes can be placed in a bone in the same spatial arrangement as the tines. In this manner, the tines 115 and 120 can be inserted into the drill holes so that the fixation device 100 can be mounted to the distal portion of the radius.

The stabilizer bar 215 stabilizes the tubes by providing a rigid mount to hold the tubes in a fixed position. The connector 230 extends from the second set of tubes 210 to the tube 225, which is placed under one of the openings 125. The connector 230 can be of any length that corresponds to the tube 225 being positioned underneath one of the openings when the fixation device 100 is placed in the drill guide 200. Like the first set of tubes 205, the tube 225 is configured to receive a drill bit to drill a hole through the radius for mounting the fixation device to the radius. The guide pins 220 are used to hold the position of the drill guide steady against the bone so that the holes that are drilled are correctly aligned. The fixation device also is used to hold the position of the drill guide steady. By inserting the tines in the second set of tubes 210, the physician can hold the first section 105 of the fixation device to maintain the position of the drill guide.

Referring to FIGS. 18 and 19, a guide 232 that is similar to the guide 200 is made by, for example, injection molding or another similar process using any biocompatible polymer, such as nylon, polyurethane, polyethylene, or polypropylene. The polymer can be loaded with a radiopaque material. In this manner, the guide will show up on X-rays if radiographic techniques are used to position the guide prior to drilling the holes to ensure accurate placement of the holes. The guide 232 includes two sets of parallel, offset tubes 233 and 234, guide pins 235, a tube 236 and a connector 237. Because the guide 232 is made of one piece, a stabilizer bar is not necessary. The guide 232 is used in the same manner as the guide 200, as described below, and can be a single use product because it is inexpensive to produce.

The guide 200 and the guide 232 optionally can be fabricated without the connector 230, 237 and tube 225, 236. In this configuration, the fixation device itself is used to hold the guide in position while drilling the holes. The guide also can be simply fabricated by injection molding as a one-piece article.

Referring to FIGS. 20–24, a disposable guide 250 can be made of a plastic body 253 and use keyed reusable metal inserts 255 that are inserted into keyed openings 257 in the plastic body. The keyed openings 257 include a wider channel 260 that receives a tubular body portion 263 of the insert 255 and a pair of narrow slots 265 that extend from the channel 260 to receive keys 267 that extend from the insert 255.

Figure 25:
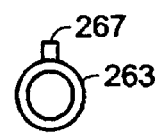
FIG. 25 is an end view of a drill insert with one key.
Figure 26:
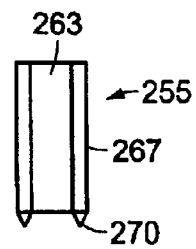
FIG. 26 is side view of the drill insert of FIG. 22 showing stabilizing prongs.

The metal inserts 255 can be configured to have one key 267, as illustrated in FIG. 25, or more than two keys. The metal insert prevents the drill bit from destroying the plastic guide body 253 when the physician is drilling holes in the bone. The keys 267 prevent the insert 255 from turning within the openings 257 when drilling the holes and, for example, the drill bit contacts the insert. The insert 255 also may have one or more prongs 270 extending from one end. In this manner, by pressing them against the bone the prongs will assist the physician in keeping the guide in position while drilling the holes in the bone.

Figure 27:
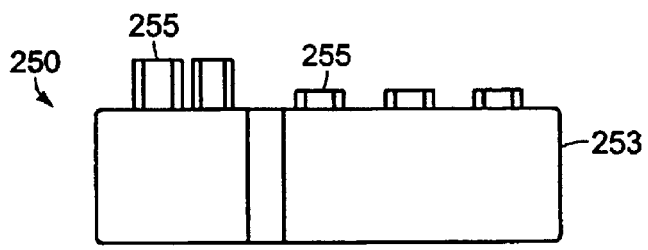
FIGS. 27 and 28 are front views of the drill guide of FIG. 20 illustrating insertion of the drill insert.
Figure 28:
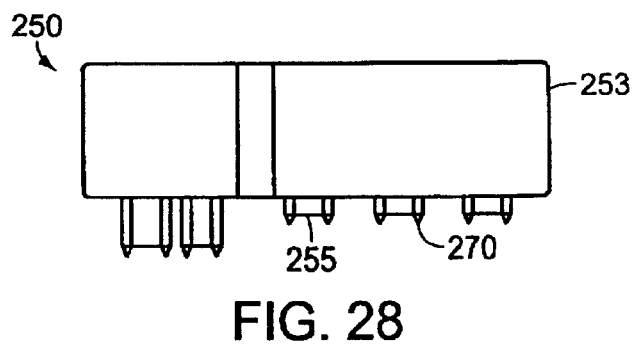

As illustrated in FIG. 27, which is a front view of the guide illustrating partial insertion of the inserts 255 into the plastic body 253, each insert is removably inserted into the openings 257. As illustrated in FIG. 28, the inserts 255 can be of different lengths so that when they are fully inserted they will mate with the surface of the distal radius. In this manner, the guide will be more firmly seated when the holes are drilled. After the holes are drilled, the inserts 255 are removed from the plastic body, cleaned, and sterilized for reuse. The plastic body 253 then is discarded or, optionally cleaned and sterilized for reuse.

Figure 29:
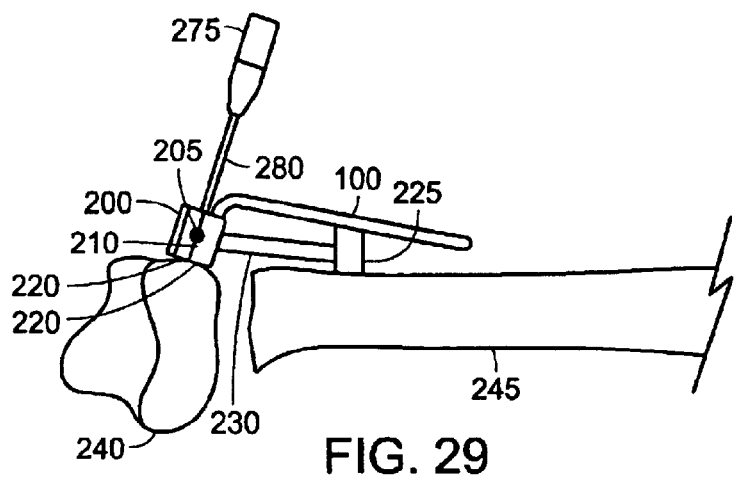
FIGS. 29 and 30 are side and top views, respectively, showing the use of the drill guide of FIGS. 16 and 17 to place the tined fixation device of FIG. 3.
Figure 30:
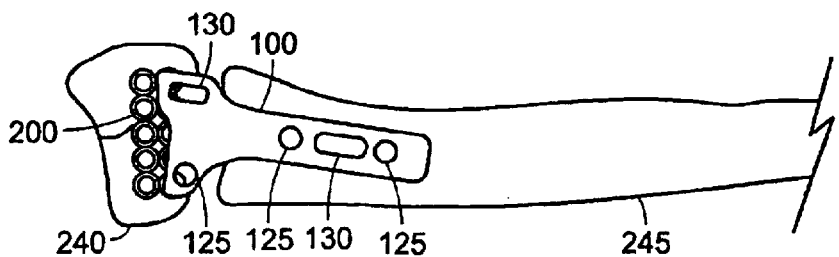

Referring to FIGS. 29 and 30, to prepare a radius for implantation of the fixation device 100, the tines 115 and 120 are placed in the second set of tubes 210 and the drill guide 200 is placed against a dorsal fragment 240 of a radius 245. The guide pins 220 protrude slightly into the bone to prevent the drill guide 200 from sliding along the surface of the bone when drilling the drill holes. The first section 105 of the fixation device then is pressed against the tube 225 such that the tube is pressed against the surface. The tube 225 optionally can include one or more pins similar to the guide pins 220 such that the position of the tube is stabilized during drilling. With the drill guide 200 firmly pressed against the radius 245 and the dorsal fragment 240, the physician uses a drill 275 and a drill bit 280 to drill holes through the first section 205 of the drill guide into the dorsal fragment. The drill guide 200 can have markings that indicate the depth to which the hole has been drilled, which allows the physician to ensure that the holes drilled are deep enough to accept the full length of each tine. Optionally, the physician can drill completely through the dorsal fragment 240 to ensure that the holes are deep enough to receive the full length of the tines.

After drilling the holes to receive the tines, the physician optionally places one or more bone screws into the bone fragments through the openings 130. The bone screws can be, for example, 4.0 mm bone screws. After placement of the tines in the bone fragments, the metaphyseal region can be bone grafted as needed, and PMMA or similar materials used to augment the distal fixation.

The physician then drills a hole into the radius through the opening underneath the tube 225. The physician also can drill holes through any of the other openings, for example, openings 125, that are on the fixation device 100. The holes drilled through the drill guide tubes 205 receive the tines to hold the dorsal fragment 240 in a fixed and stable position relative to the rest of the radius 245. The holes drilled through the openings and the tube 225 are used for passing through tensioning devices or connectors to mount the fixation device 100 to the radius 245 and the dorsal fragment 240. The implantation of a fixation plate is described in U.S. Pat. No. 5,586,985 to Putnam. That disclosure and the patent itself are incorporated herein in their entirety by reference.

Figure 31:
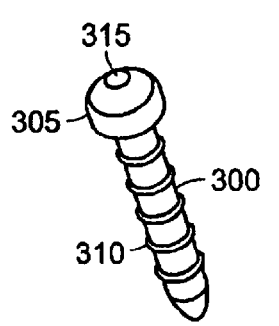
FIG. 31 is a perspective view of a gimbal-shaped bone screw for use with the fixation device of FIG. 3.
Figure 32:
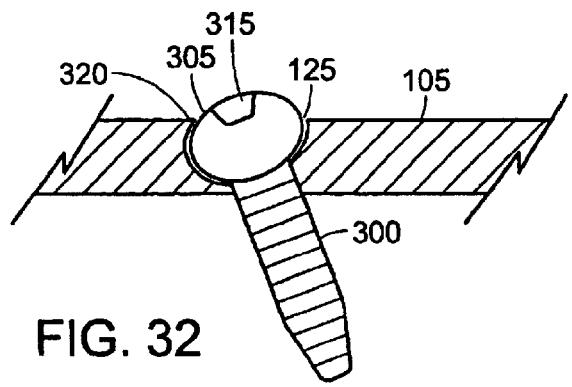
FIG. 32 is a cross-section side view of the bone screw of FIG. 31 inserted in the fixation device.

The connectors can be in the form of any device that functions to mount the fixation device 100 to a bone. For example, conventional bone screws can be used. Referring to FIGS. 31 and 32, a gimbal screw 300 can be used with the fixation device 100. The gimbal screw 300 includes a gimbal-shaped head 305, a threaded shank 310, and a mating end 315 that is configured to mate with, for example, a hexagonal allen wrench or a Phillips head screw driver. The openings in the fixation device 100 can be rounded to mate with the gimbal-shaped head 305 of the screw. With this configuration, the head 305 is movable within the opening to orient the screw 300 into the bone over a range of angles. This allows the physician to angle the screw to accommodate various bone anatomies.

Figure 33:
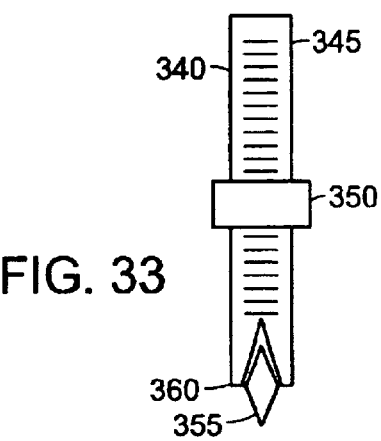
FIG. 33 is a side view of a tie-band fastener for use with the fixation device of FIG. 3.
Figure 34:
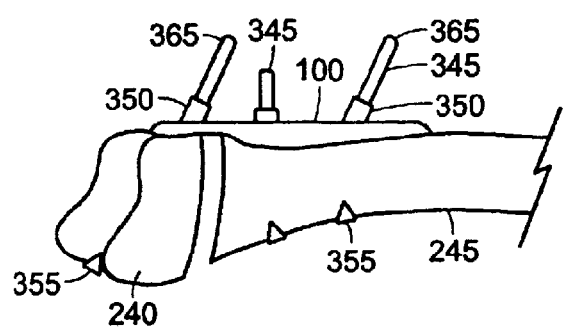
FIG. 34 is a side view of the tie-band fastener of FIG. 33 used to fasten the fixation device to a radius and dorsal fragment.

Referring to FIG. 33, the tensioning device can be implemented as a tie band fastener 340 that includes a tie band 345, a slidable tab 350, and a stop 355. The slidable tab 350 is configured to slide in one direction along the tie band 345 using techniques that are well-known in the art. The stop 355 is positioned at the end of the tie band 345 and may be pivotally attached to a bar 360 such that the stop can be aligned with or perpendicular to the tie band. As illustrated in FIG. 34, to use the tie band fastener 340, the stop 355 and adjacent end of the tie band 345 are inserted through one of the openings in the fixation device 100 and into a pre-drilled hole through the radius 245 or the distal fragment 240. Once the stop passes through the hole, the physician pulls back the tie band so that the stop 355 will pivot into a position that is perpendicular to the tie band and pressed against the bone. In this configuration, the tie band fastener 340 cannot be pulled back out of the hole. The slidable tab 350 then is pushed down along the tie band 345 until it is firmly against the fixation device 100. A portion 365 of the tie band that extends beyond the slidable tab 350 is cut and discarded.

A number of variations on the tie band can be used as a tensioning device to hold the device to a bone. For example, referring to FIGS. 35–38, a fastener 400 can be configured with a rounded base 405 to angulate within the openings 125 in the device 100, 150 and a flat top 410 to be generally flush with the outer surface of the device 100, 150. The fastener 400 also can have a recess 415 in the top 410 so that the tie band 345 can be cut and the remaining end can be positioned within the recess. In this manner, the remaining end will not be in contact with tissue, which can be irritable to the tissue and/or painful if there is substantial movement of the tissue against the remaining end. The fastener 400 also includes a channel 420 passing between the base 405 and the top 410 and which is ribbed to allow movement of the tie band in one direction. Referring to FIGS. 39 and 40, the fastener 400 can be configured to have an extension 425 protruding from the rounded base 405. The extension provides extra land for retaining the tie band, which provides a more secure placement of the tie band in the fastener 400.

Referring to FIGS. 41–44, a molly bolt system 450 also can be used as a tensioning device to hold the device 100 to the radius. The molly bolt system 450 includes a head 455, a nut 460, and one or more flexible arms 465. Each arm 465 includes a first length portion 470, a second length portion 473, and a third length portion 475. The nut 460 is threaded such that when a physician inserts a screw 477 through the head 455 into the nut, tightening the screw will pull the nut towards the head. The arms 465 can be formed with weakening notches 480 at predetermined positions that will cause the arms to have a tendency to bend or fold at those positions during tightening of the screw. The second length portion 473 and the third length portion 475 are offset from each other so that when they are folded together, they form a flat surface with a low profile.

The notches 480 can be placed such that the first length portion 470 is in the radius and the second length portion 473 and the third length portion 475 are configured to fold up against or adjacent to each other when the nut 460 is tightened and pulled towards the head. By estimating the diameter of the radius from a radiograph, the physician can form a notch 480 at a position on the first length portion 470 that corresponds to the edge of the channel in the bone from which the nut 460 will protrude. The second length portion 473 and the third length portion 475 also can be notched to fold over, or adjacent to, each other and form an obstacle to completely pulling the nut 460 into the channel, although it may be somewhat recessed into the channel. As shown in FIGS. 41 and 42, the second length portion 473 and the third length portion 475 are offset so that they will be adjacent to each other when they are bent. Moreover, as illustrated in FIG. 43, the molly bolt system 450 advantageously can be used to set the position of the bone fragments relative to each other by the degree to which the nut 460 is tightened towards the head 455.

Alternatively, as illustrated in FIG. 44, the molly bolt can be configured so that the second length portion 473 and the third length portion 475 are configured to overlap when folded together to provide a more rigid member to resist pulling into the channel through the bone.

Figure 45:
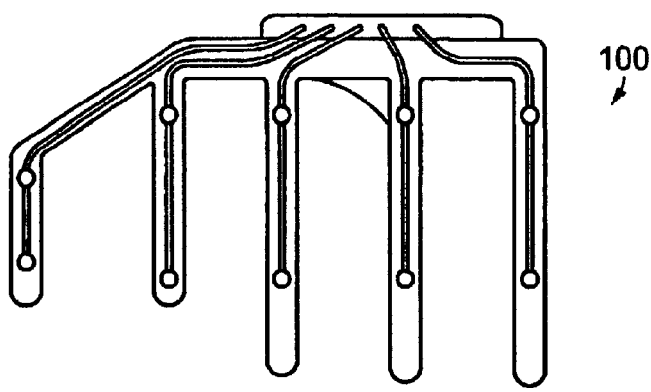
FIG. 45 is front view of the fixation device of FIG. 3 with strain gauges on the tines.
Figure 46:
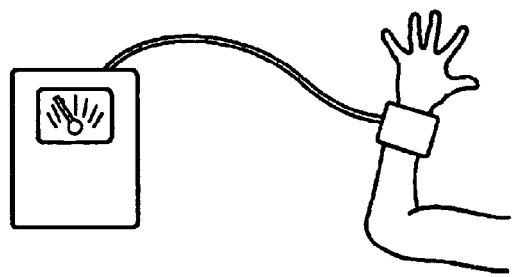
FIG. 46 is a front view of a tensiometer used to measure the strain on the tines.

Referring to FIGS. 45 and 46, the device 100 can be modified to include one or more tensiometers 500 mounted to the tines and electrically connected to a transmitter 505 that is mounted to the device 100 or is left in a subcutaneous pocket on the patient's arm. The tensiometers 500 can be implemented as strain gauges that provide a measure of the amount of strain on one or more of the tines. The physician can monitor the trend of strain over time until the strain value appears to be unchanging, which is indicative of adequate healing. To measure the strain, a monitor 510 can be placed over the transmitter and used to remotely turn on and off the transmitter and to monitor the strain values.

Figure 47:
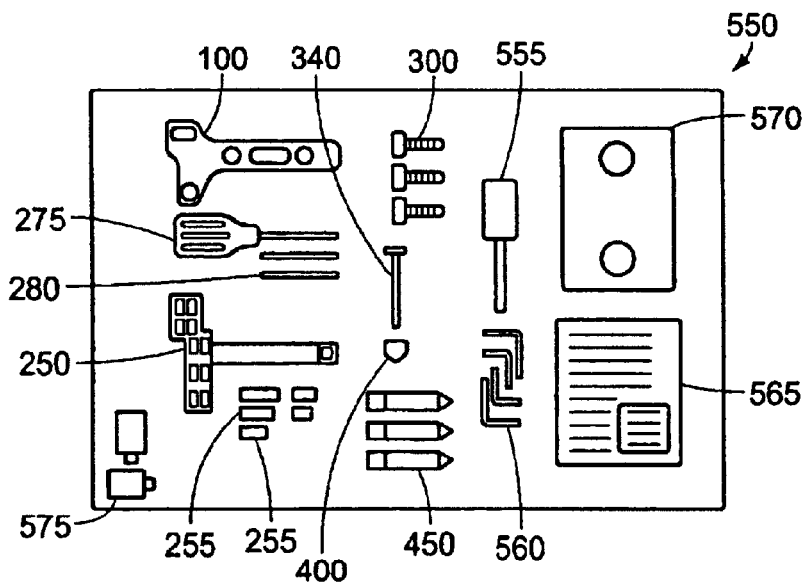
FIG. 47 is a top view of a fixation device kit.

Referring to FIG. 47, a fixation plate kit 550 is configured to include the fixation plate 100 and other tools necessary to perform the implantation. For example, the kit 550 can include the drill 275; the guide 250; drill bits 280 covering a range of sizes; tensioning devices, such as bone screws 300, molly bolts 450, tie bands 340, tie band fasteners 400; a screw driver 555 to place the bone screw; a set of allen wrenches 560; instructions for use 565; an instructional video 570; and/or therapeutic agents 575 to apply to the device or to the injury site. The therapeutic agents can be a bone growth regulating protein and/or a platelet derived growth factor. Providing these items in a kit form is advantageous to the physician because there is no need to search for or attain overlooked items that may be necessary for the procedure because all of the items are included. Providing an instructional video with the kit or separately is advantageous to the physician because the physician can view the video as often as necessary until the required degree of comfort and confidence in performing the procedure is attained to actually undertake the procedure. By providing the items necessary to perform the procedure and the instructional video and instructions for use together provide advantages to physicians because the required learning and understanding can be quickly attained while manipulating and examining the necessary articles needed for the procedure.

Figure 48:
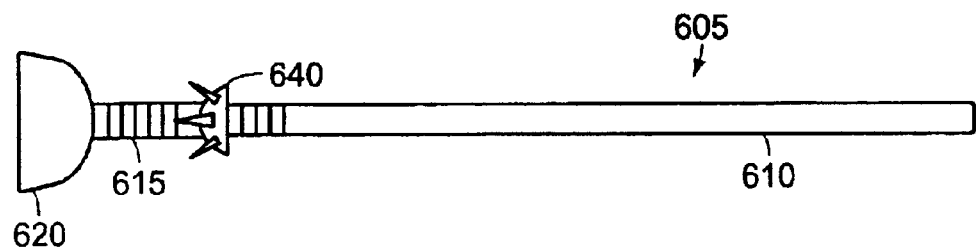
FIG. 48 is a side view of an articulating tine.
Figure 49:
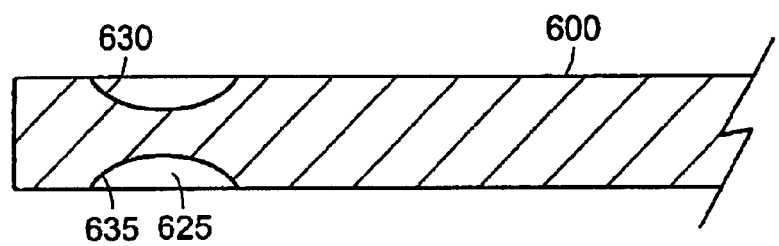
FIG. 49 is a cross-sectional side view of a fixation plate having radiused openings to receive the articulating tine of FIG. 48.
Figure 50:
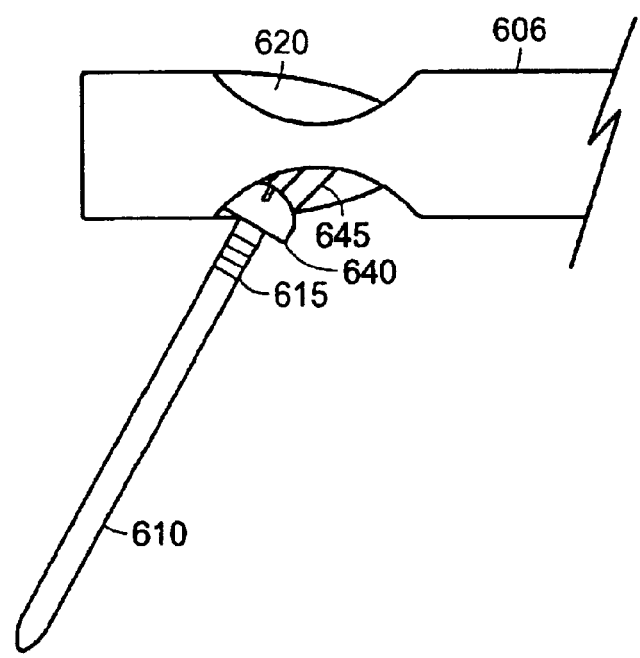
FIG. 50 is a side view of the articulating tine mounted in the fixation plate of FIG. 49.

A number of embodiments have been described. Nevertheless, it will be understood that various modifications may be made without departing from the spirit and scope of the invention. For example, referring to FIGS. 48–50, a tined fixation plate 600 can be fabricated with non-integral tines or articulating members to accommodate extremely complicated fractures where there are numerous bone fragments. For example, a tine 605 can be configured as an articulating screw having a non-threaded length 610, a threaded length 615, and a head 620. The plate 600 can be fabricated to have each opening 625 radiused on the topside and on the bottom side. The topside opening radius 630 allows the head 620 to be moved over multiple angles and orientations. The bottom side opening radius 635 permits the non-threaded length 610 and the threaded length 615 to likewise move to the multiple angles and orientations. A curved nut 640 slidably articulates within the bottom side opening radius 635. By turning the tine 605, for example with a screw driver or allen wrench, the plate 600 is pinched between the head 620 and the nut 640 and the position of the tine 605 can be fixed. The nut 640 can include flexible prongs 645 that will press against the bottom side opening radius 635 to cause friction that will allow the nut to be tightened against the plate without having the nut move when the head is turned.

Figure 51:
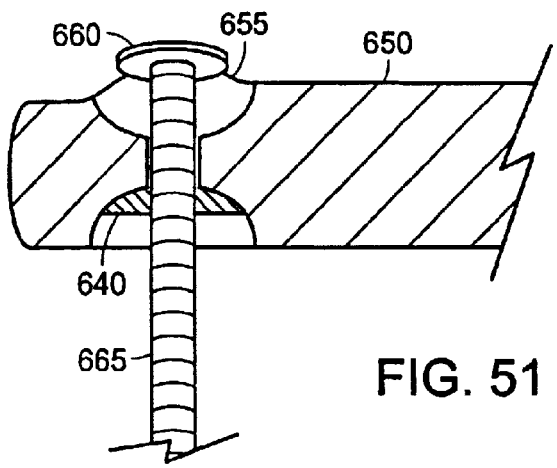
FIG. 51 is a cross-sectional side view of an articulating tine with a round head mounted in a fixation plate.
Figures 52, 53:
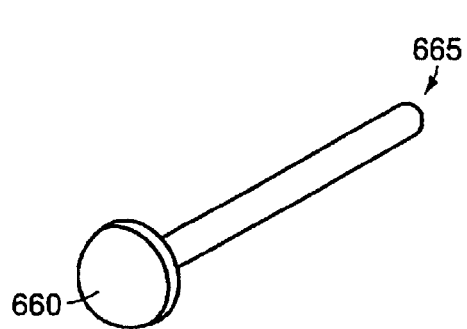
FIGS. 52 and 53 are perspective and side views, respectively, of the articulating tine of FIG. 51.
Figure 54:
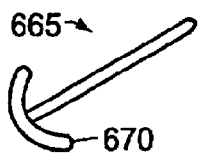
FIGS. 54 and 55 are perspective and side views, respectively, of an articulating tine having an elongated head.
Figure 55:
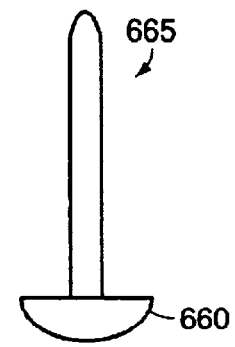
Figure 56:
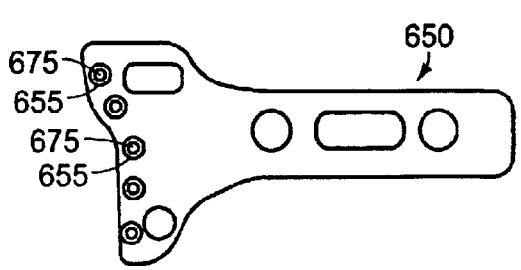
FIGS. 56 and 57 are top and side views, respectively, of the fixation plate of FIG. 51.
Figure 57:
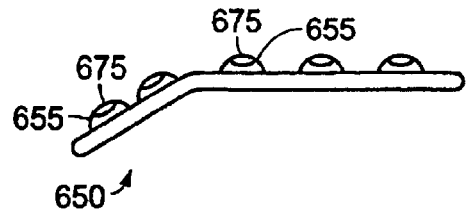
Figure 58:
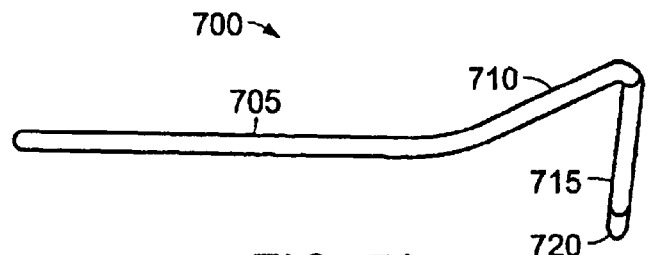
FIG. 58 is a side view of a fixation plate for fixation of the volar surface of the distal radius.
Figure 59:
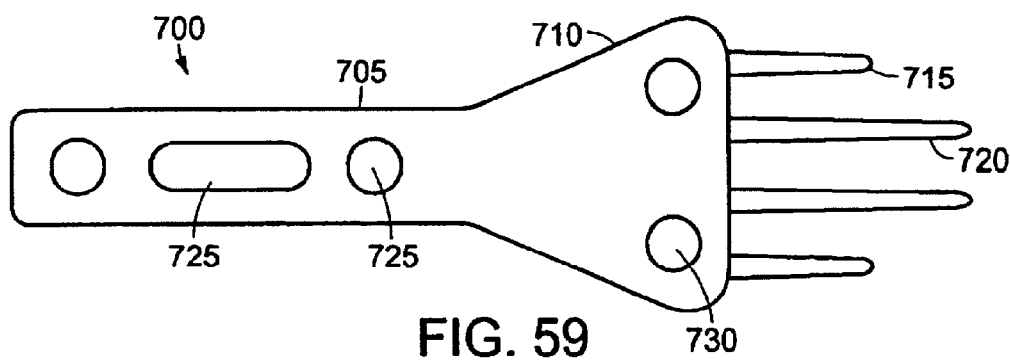
FIG. 59 is a top view of the fixation plate of FIG. 58.
Figure 60:
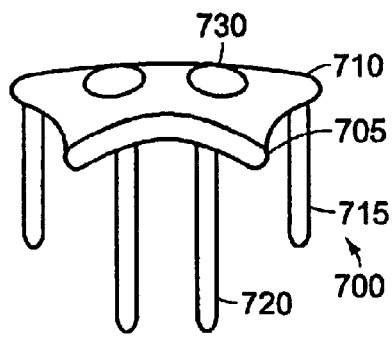
FIG. 60 is an end view of the fixation plate of FIG. 58.
Figure 61:
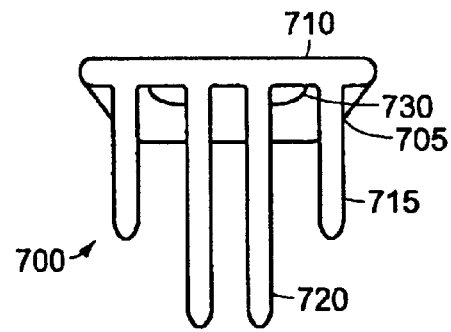
FIG. 61 is a front view of the fixation plate of FIG. 58.
Figure 62:
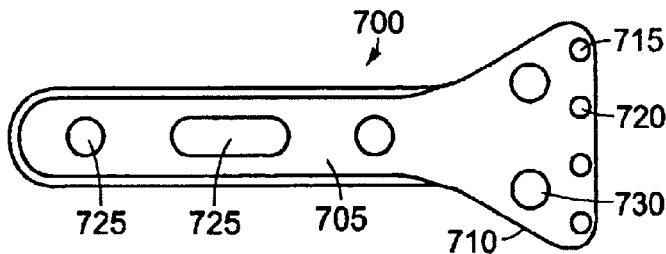
FIG. 62 is bottom view of the fixation plate of FIG. 58.

As illustrated in FIGS. 51–53, which illustrates a second implementation of a fixation plate with non-integral tines or articulating members, a fixation plate 650 has rounded ridges 655 over which articulate matching rounded or hemispherically shaped heads 660 on the articulating tines 665. As illustrated in FIGS. 54 and 55, the articulating tines 665 can be fabricated with elongated, rounded heads 670. As illustrated in FIGS. 56 and 57, the rounded ridges 655 having openings 675. These openings 675 can be configured to have a large or a small diameter, to be generally elongated, or be of any shape such that the head 660, 670 can articulate over the rounded ridges without being pulled into the opening 675.

Figure 1:
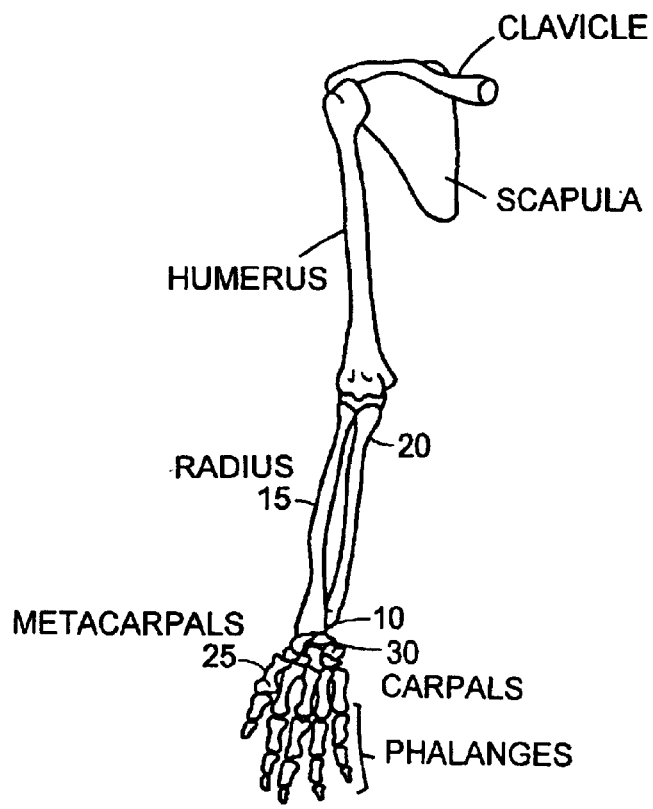
FIG. 1 is a front view of the anatomy of a human arm.
Figure 2A:
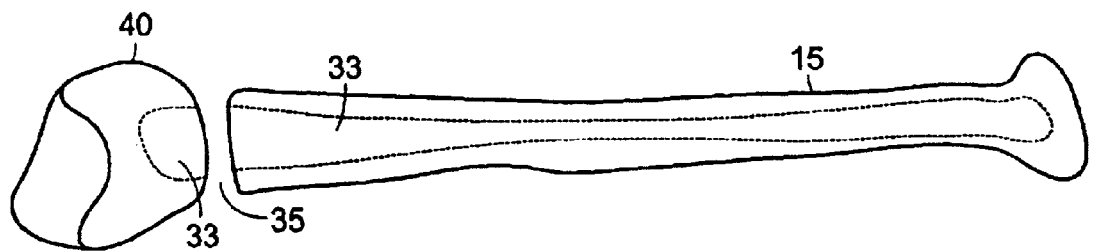
FIG. 2a is a side view of a distal radius fracture.
Figure 2B:
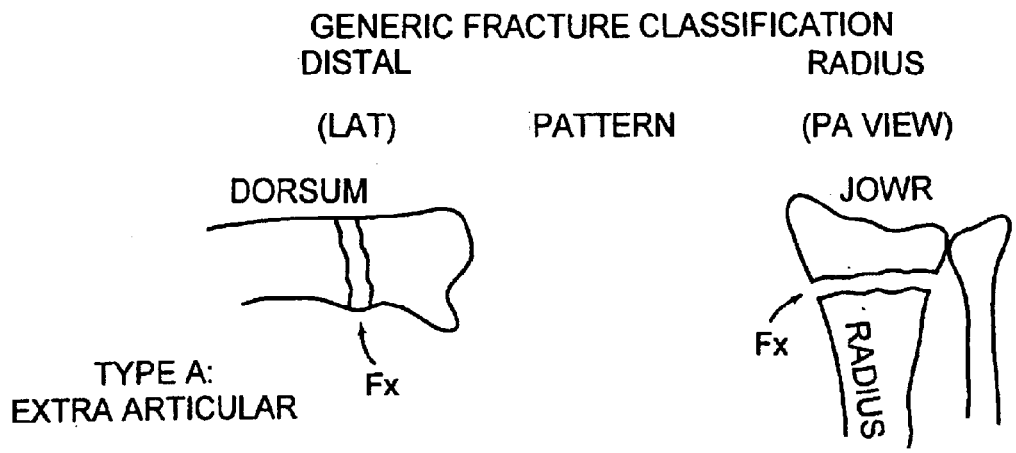
FIGS. 2b–d are side views of different types of distal radius fractures classified according to the OTA classification system.
Figure 2C:
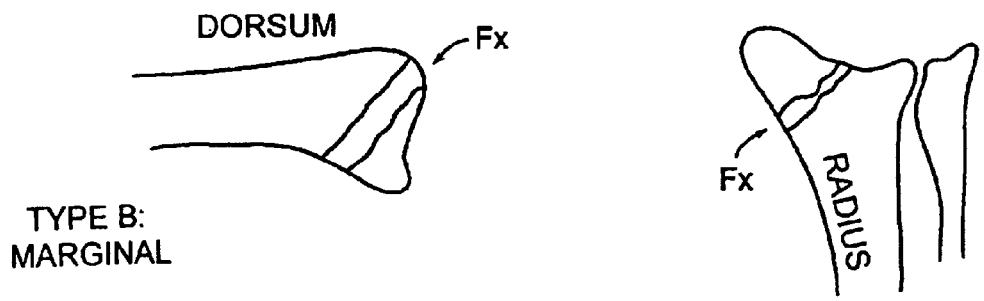
Figure 2D:
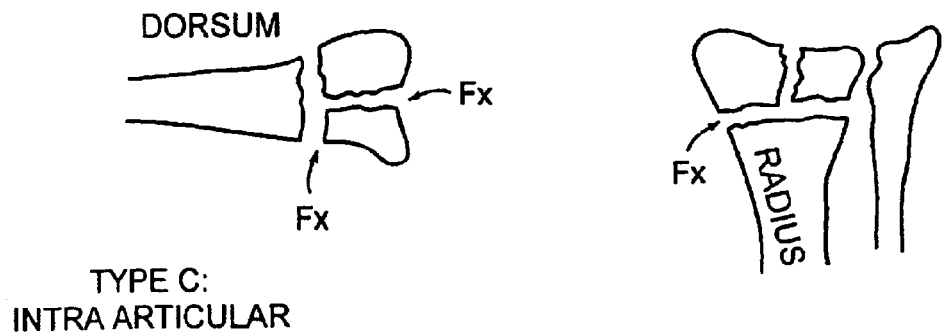
Figure 3:
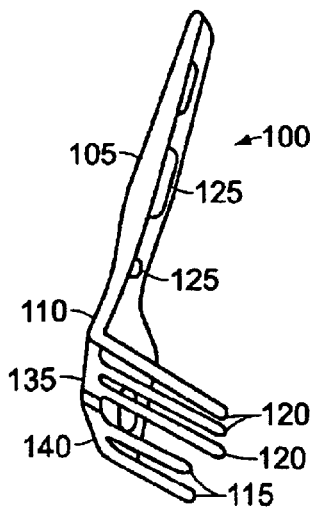
FIG. 3 is a perspective view of a tined fixation device for fixation of a left wrist fracture.
Figure 4:
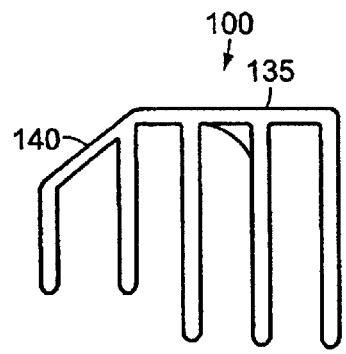
FIGS. 4 and 5 are front and end views, respectively, of the tined fixation device of FIG. 3.
Figure 5:
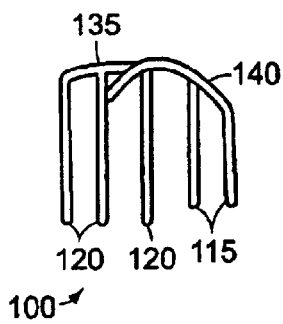

Referring to FIGS. 58–62, the tined fixation plate described above can be configured specifically as a distal radius volar fixation plate 700, namely, a fixation plate for placement on the volar surface of the distal radius to fix a fracture of the distal radius. Moreover, any and all of the techniques and devices related to fixation plates described above can be applied to the distal radius volar fixation plate 700. A primary design difference between a tined plate for distal radius dorsal fixation and distal radius volar fixation is the angle between the proximal portion and the distal portion of the plate and results from the anatomical differences between the distal dorsal radius and the distal volar radius (FIG. 2a). For example, the volar anatomy includes a sharper angle in the transition between the length of the radius and the distal head of the radius. As such, the volar fixation plate 700 includes a first or proximal section 705 and a second or distal section 710 at an angle to the proximal section and from which the tines 715 and 720 extend.

The first section 705 is generally elongated, narrower than the second section 710, and includes one or more openings 725. The openings 725 are used to mount the first section to the volar surface of the radius, and may be round, elongated, and/or of any other shape, and of varying sizes, as described above, such as a pair of round openings and an elongated opening. The elongated opening provides flexibility for screw placement. The openings 725 also may be oversized to allow screws to be angulated and countersunk full thickness for a low profile. The first section 705 has a curved shape across its width that is designed to generally follow the typical curve of the volar surface of the radius on which it will be mounted so that the first section will be stably seated against the volar surface of the radius.

Figure 63:
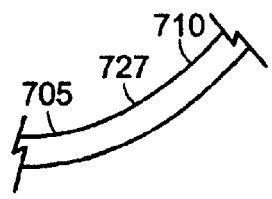
FIG. 63 is a side view of a transition zone of the fixation plate of FIG. 58.
Figure 64:
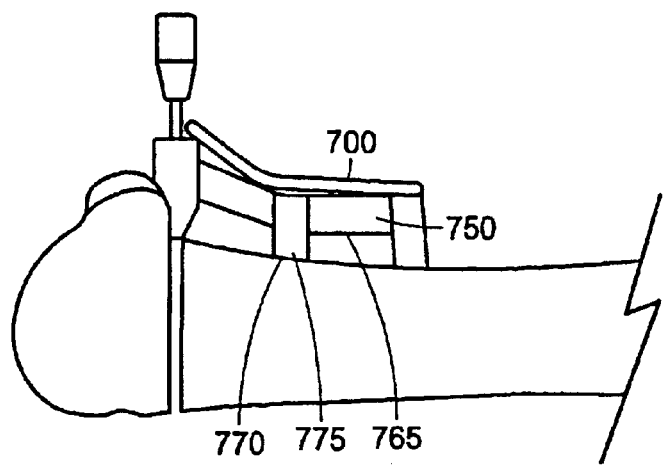
FIG. 64 is a side view showing the implantation of the fixation plate of FIG. 58.
Figure 65:
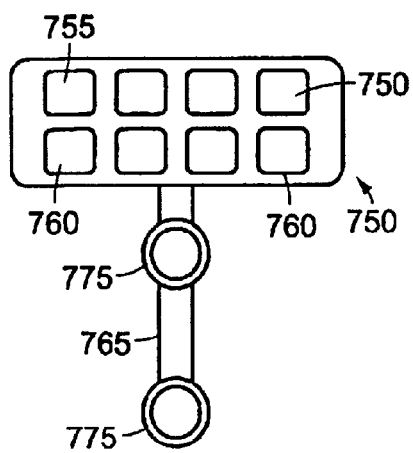
FIGS. 65 and 66 are top and side views, respectively, of a guide for implanting the fixation plate of FIG. 58.
Figure 66:
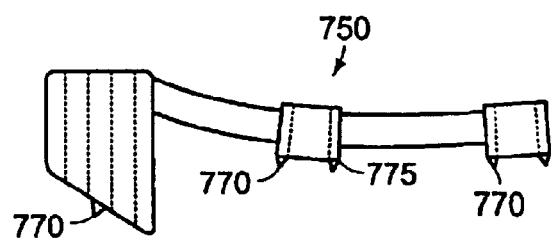
Figure 67:
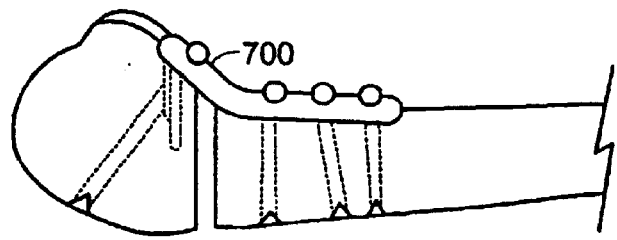
FIG. 67 is a side view of the fixation plate of FIG. 58 mounted to the volar surface of a distal radius fracture.

The second section 710 forms a generally T-shaped configuration with the first section 705 and forms an angle with the first section such that the second section follows the volar configuration of the distal head of the radius. The angle between the first section 705 and the second section 710 may be, for example, between approximately 5° and 45°, and more particularly, between 10° and 30°, and even more particularly, between approximately 10° and 20°. The first section 705 can transition abruptly or gradually to the second section 710. For example, FIG. 63 illustrates a transition zone 727 between the first section 705 and the second section 710 that provides a gradual transition between the segments. Fixation plates 710 can be fabricated with a range of transition angles (e.g., in increments of, for example, 2° to 5°) and the physician can use a radiograph to determine the appropriate angle of the fixation plate to use on a particular patient based on the patient's volar radius anatomy.

The second section 710 also includes openings 730. The second section is generally flat such that it generally follows the generally flat shape of the volar surface of the distal radius. The tines 715 and 720 extend from the second section 710. Although FIGS. 58–62 show the tines 715 and 720 extending from the end of the second section 710, the fixation device 700 can be configured with the tines extending from a more central portion of the second section such that the second section extends beyond the tines to add stability to the distal portion of the volar surface of the radius. The tines 715 and 720 extend at an angle from the second section 710 but are generally perpendicular to the first section 705, although a range of angles around the perpendicular is permissible. For example, the angles can range from between approximately 75° and 115° and more particularly between approximately 85° and 105°.

The tines 715 and 720 are of different lengths, with the outer tines 715 being of a shorter length than the inner tines 720. This difference in length results from the generally round shape of the distal head of the radius and corresponds to the thickness of the distal radius from the volar portion of the radius such that the tines can be as long as possible to provide the maximum fixation and stabilization. In this example, the fixation device 700 is configured to have two tines 715 and two tines 720 but other configurations with more or fewer tines are possible. For example, the fixation device can be configured to have two shorter tines 715 and one longer tine 720. Moreover, the tines 715 and 720 can be configured to be of the same length, for example, for ease of manufacturing.

Referring to FIGS. 64–67, the fixation plate 700 can be implanted on the volar surface of the distal radius by drilling holes in the radius to receive the tines. Although the holes can be drilled in a free hand manner, a drill guide 750 may be used to drill holes that are accurately aligned with the configuration of the fixation device 700 and, more specifically, with the configuration of the tines 715 and 720. The drill guide includes a first set of tubes or openings 755, a second set of tubes, openings, or tine covers 760, a bar 765, guide pins 770, and one or more drill tubes 775 for aligning openings in the radius. The bar 765 is generally perpendicular to the tubes 755 and 760. Each set of tubes 755 and 760 is arranged to resemble the arrangement of the tines 715 and 720. The first set of tubes 755 is configured to receive drill bits when the tines 715 and 720 are inserted into the second set of tubes 760 such that drill holes can be placed in the volar surface in the same spatial arrangement as the tines. In this manner, the tines 715 and 720 can be inserted into the drill holes so that the fixation device 700 can be mounted to the volar surface of the distal portion of the radius. The drill tubes 775 are used to align the drill for mounting the first section 705 of the fixation plate to the radius on the proximal side of the fracture. The guide pins 770 are used to firmly position the guide 750 against the bone's surface while the holes are being placed. The guide 750 can be fabricated using any of the techniques and materials described above or any combination of the techniques and materials described above.

The fixation plate 700 is mounted to the radius using any of the fixation devices described above by drilling openings or channels into the radius using any of the techniques described above. After the tines are placed in openings in the distal radius, fixation or tensioning devices are passed through the openings 725 and 730 in the fixation plate, passed through the openings or channels in the radius, and then tightened to ensure that the plate is secured to the radius. The fixation or tensioning devices ensure that the fixation plate will not come loose from the radius and the tines ensure that the fractured portion of the distal radius will not move away from the rest of the radius or be loose and move relative to the radius, both of which could prevent or delay healing of the fracture.

Figure 68:
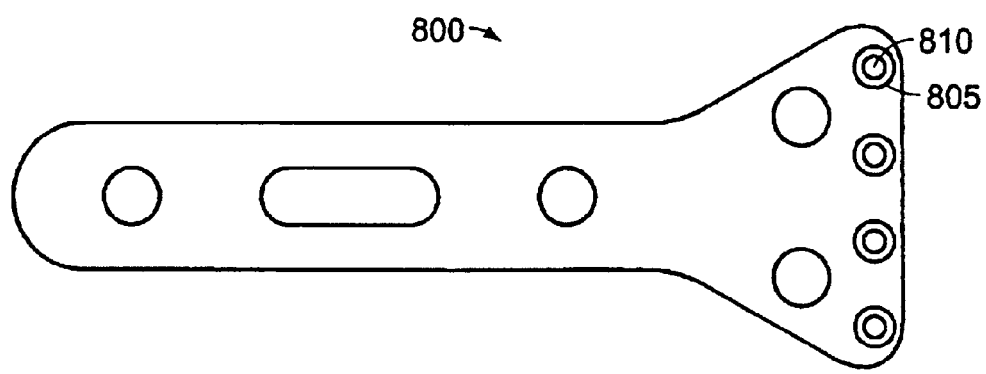
FIGS. 68 and 69 are top and side views, respectively, of a fixation plate having radiused openings to receive articulating tines.
Figure 69:
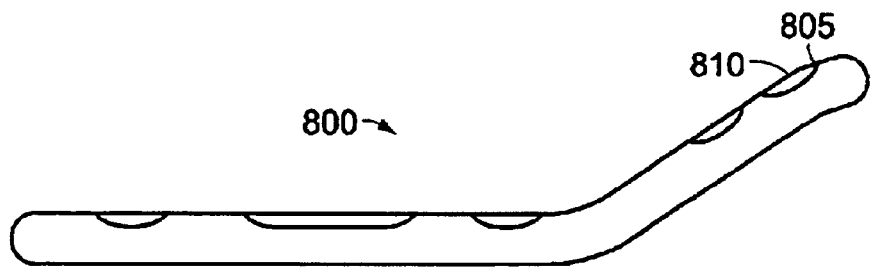
Figure 70:
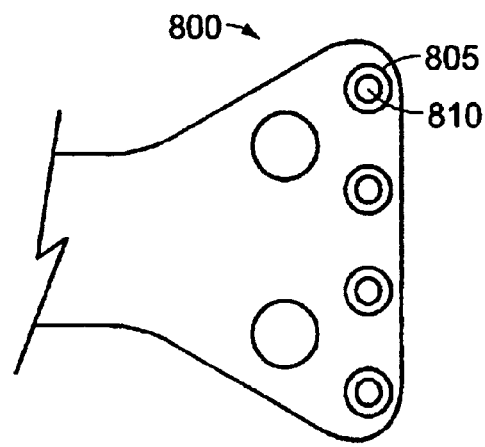
FIG. 70 is a top view of the radiused openings of the fixation plate of FIG. 68.

Referring to FIGS. 68–70, the fixation plate for the volar surface of the distal radius can be configured to use removable or non-integral tines (i.e., articulating members) using any of the tines and methods described above. For example, a fixation plate 800 that is configured to use non-integral tines (i.e., articulating members) differs from the fixation plate 700 by including rounded ridges 805 over which articulate matching rounded or hemispherically-shaped heads 660 on the articulating tines 665 (FIGS. 52 and 53). The articulating tines 665 also can be fabricated with elongated, rounded heads 670 (FIGS. 54 and 55). As illustrated in FIGS. 68–70, the rounded ridges 805 having openings 810 through which the articulating tines 665 extend. These openings 810 can be configured to have a large or a small diameter, to be generally elongated, or be of any shape such that the head 660, 670 can articulate over the ridges 805 without being pulled into or passed through the opening 810.

Other embodiments are within the scope of the following claims.

What is claimed is:

1. A fixation plate kit for fixation of a distal radius fracture, the kit comprising:
   a fixation plate comprising an elongated plate having a distal portion and a proximal portion, the distal portion including a first surface, a second surface extending from and forming an angle with the first surface, and at least one tine extending from the first surface, the proximal portion having a length and a width and being generally curved across its width along its length and including at least one opening configured to receive a tensioning device; and
   a matching tensioning device configured to pass through the opening in the proximal portion, through a channel in a radius, and to be tightenable to fix the proximal portion to the radius.

2. The fixation plate kit of claim 1 further comprising a screw configured to be inserted into bone tissue, wherein the distal portion of the fixation plate includes a second opening configured to receive the screw.

3. The fixation plate kit of claim 2 wherein the second opening includes a radiused circumference and the screw includes a curved gimbal head configured to articulate against the radiused circumference.

4. The fixation plate kit of claim 2 wherein the screw is a bicortical screw.

5. The fixation plate kit of claim 2 wherein the screw is a unicortical screw.

6. The fixation plate kit of claim 1 wherein the tensioning device comprises a shaft having an interlocking interface, a head, and a moveable lock configured to move in one direction along the shaft towards the head.

7. The fixation plate kit of claim 6 wherein the head has a curved surface configured to articulate in a curved surface of the opening in the proximal portion.

8. The fixation plate kit of claim 1 wherein the tensioning device comprises a molly bolt.

9. The fixation plate kit of claim 1 further comprising a drill bit configured to drill a hole in bone tissue.

10. The fixation plate kit of claim 1 further comprising a guide for drilling holes in bone to place the tine, the guide comprising at least one dill guide and at least one tine cover, wherein the at least one drill guide is configured to receive, orient, and offset a drill bit in the same orientation as the tine when the tine is inserted into the at least one tine cover.

11. The fixation plate kit of claim 10 wherein the at least one drill guide includes at least one opening and an insert configured to be received in the opening.

12. The fixation plate kit of claim 1 further comprising written instructions for use.

13. The fixation plate kit of claim 1 further comprising an instructional video.

14. The fixation plate kit of claim 1 further comprising a tensiometer mounted to the tine and configured to measure a tension in the tine.

15. The fixation plate kit of claim 1 further comprising a monitor, wherein the tensiometer transmits a signal indicative of strain in the tine and the monitor is configured to receive the signal.

16. The fixation plate kit of claim 1 wherein the fixation plate includes a therapeutic agent.

17. The fixation plate kit of claim 16 wherein the therapeutic agent comprises one or both of a bone growth regulating protein and a platelet derived growth factor.

18. The fixation plate kit of claim 1 wherein the kit further comprises one or both of a screw driver and an alien wrench.

19. The fixation plate of claim 1 wherein the elongated plate is configured to be fixed to the dorsal surface of the distal radius.

* * * * *

UNITED STATES PATENT AND TRADEMARK OFFICE
CERTIFICATE OF CORRECTION

PATENT NO. : 6,755,831 B2 Page 1 of 1
DATED : June 29, 2004
INVENTOR(S) : Matthew D. Putnam, David Gesensway and Charles D. Jennings It is certified that error appears in the above-identified patent and that said Letters Patent is hereby corrected as shown below:

<u>Title page,</u>
Item [57], ABSTRACT,
Line 1, please delete "facture" and insert -- fracture -- therefore;

<u>Column 14,</u>
Line 26, please delete "dill" and insert -- drill -- therefor;
Line 50, please delete "alien" and insert -- allen -- therefor.

Signed and Sealed this

Fifth Day of April, 2005

JON W. DUDAS
*Director of the United States Patent and Trademark Office*